United States Patent
Wang et al.

(10) Patent No.: US 12,194,145 B2
(45) Date of Patent: Jan. 14, 2025

(54) SiRNA DELIVERY SYSTEM COMPOUND AS WELL AS PREPARATION METHOD AND APPLICATION THEREOF

(71) Applicant: ZHENGZHOU UNIVERSITY, Zhengzhou (CN)

(72) Inventors: Zhimin Wang, Zhengzhou (CN); Chengshen Zhu, Zhengzhou (CN); Wentao Liu, Zhengzhou (CN); Xiangyang Zhang, Zhengzhou (CN); Suqin He, Zhengzhou (CN); Yaohe Wang, Zhengzhou (CN); Hao Liu, Zhengzhou (CN); Miaoming Huang, Zhengzhou (CN); Chenglin Zhang, Zhengzhou (CN); Bin Qin, Zhengzhou (CN); Lei Huang, Zhengzhou (CN)

( * ) Notice: Subject to any disclaimer, the term of this patent is extended or adjusted under 35 U.S.C. 154(b) by 948 days.

(21) Appl. No.: 17/227,408

(22) Filed: Apr. 12, 2021

(65) Prior Publication Data
US 2022/0062191 A1    Mar. 3, 2022

(30) Foreign Application Priority Data
Jun. 30, 2020    (CN) .......................... 202010613003.8

(51) Int. Cl.
| | |
|---|---|
| *A61K 9/127* | (2006.01) |
| *A61K 9/51* | (2006.01) |
| *A61K 31/713* | (2006.01) |
| *B82Y 5/00* | (2011.01) |
| *C08B 37/08* | (2006.01) |

(52) U.S. Cl.
CPC ............ *A61K 9/127* (2013.01); *A61K 9/5161* (2013.01); *B82Y 5/00* (2013.01); *C08B 37/003* (2013.01); *A61K 31/713* (2013.01)

(58) Field of Classification Search
None
See application file for complete search history.

(56) References Cited

U.S. PATENT DOCUMENTS 8,999,351 B2 * 4/2015 Manoharan ............ A61K 47/44
424/204.1

OTHER PUBLICATIONS

Oh. Advanced Drug Delivery Reviews, 2009, 61, pp. 850-862, available online May 5, 2009 (Year: 2009).*
Tatiparti. Nanomaterials, 2017, 7, 77, pp. 1-17, published Apr. 5, 2017 (Year: 2017).*

* cited by examiner

Primary Examiner — Noble E Jarrell
(74) Attorney, Agent, or Firm — Addison D. Ault; IPGentleman Intellectual Property Services, LLC (57) ABSTRACT

The invention relates to the technical field of gene treatment and nano targeted delivery, in particular to a siRNA delivery system compound as well as a preparation method and application thereof. The preparation method comprises the following steps of reacting Boc-protected histidine with cholesterol to generate Boc-protected histidine cholesteryl ester, and removing BOC-released protected amino in trifluoroacetic acid to generate histidine cholesteryl ester; then, enabling amino to react with carboxyl of carboxymethyl chitosan to modify long-chain carboxymethyl chitosan to generate carboxymethyl chitosan modified by histidine cholesteryl ester, and performing targeted labeling on carboxymethyl chitosan modified by histidine cholesteryl ester to generate a carboxymethyl chitosan high-molecular compound modified by histidine cholesteryl ester and a targeted marker together, then forming a stable spherical delivery vector through self-assembly above critical micelle concentration, and mixing the stable spherical delivery vector with siRNA (small interfering ribonucleic acid) to obtain the siRNA delivery system compound.

4 Claims, 6 Drawing Sheets
Specification includes a Sequence Listing.

SEQUENCE LISTING

```
<160> NUMBER OF SEQ ID NOS: 1

<210> SEQ ID NO 1
<211> LENGTH: 21
<212> TYPE: RNA
<213> ORGANISM: Artificial Sequence
<220> FEATURE:
<223> OTHER INFORMATION: Synthesized

<400> SEQUENCE: 1
uggauuugua ccauucuucu g                                                 21
```

SiRNA DELIVERY SYSTEM COMPOUND AS WELL AS PREPARATION METHOD AND APPLICATION THEREOF

BACKGROUND OF THE INVENTION

1. Field of the Invention

The invention relates to the technical field of gene therapy and nano-targeted delivery, in particular to a siRNA delivery system compound as well as a preparation method and application thereof.

2. Description of the Related Art

RNA interference is a mechanism left over from the evolution of biology that regulates gene expression through siRNA after transcription. The reason why RNA interference has attracted widespread attention in almost all research fields in the biomedical community is not only because in theory, basically any gene in human cells can be silenced by siRNA, but also because siRNA has a powerful effect of inhibiting gene expression and a high degree of sequence specificity. The powerful silencing effect of siRNA is manifested in the tens to thousands of times the gene silencing efficiency compared with traditional tools such as antisense oligonucleotides and ribozymes to inhibit gene expression. The high sequence specificity of siRNA is manifested in that the gene silencing effect of siRNA which is one base sequence different from the target gene mRNA will be greatly weakened, thereby ensuring the high specificity of suppressing the target gene. Therefore, siRNA, as a promising gene targeting drug, can be widely used in the treatment of genetic diseases such as cancer. However, due to the low stability and poor pharmacokinetics of siRNA and various biological barriers in the body, siRNA has poor therapeutic effects in vivo. Therefore, how to maintain the stability of the siRNA delivery process, the accumulation of effective therapeutic doses in target tissues, and the efficient internalization of cells are still the main problems that limit the clinical transformation and large-scale application of siRNA.

In organisms, especially in humans, any level of biological barrier has an important influence on the therapeutic effect of drugs. After the injected drugs are cleared and retained by barriers at all levels, the drugs that finally reach the site of action and enter specific cells are only about 0.7% of the injected amount. This explains why drug therapy, especially chemotherapy for tumors, has relatively large side effects, strong body immune response, and poor therapeutic effect. On the other hand, it also shows that even though researchers have designed various nanocarriers with multiple functions, they cannot meet the requirements of overcoming each level of biological obstacles in the body at the same time, so that the final better therapeutic effect cannot be achieved. Therefore, it is necessary to re-optimize various designs to give the nano-drug carrier tumor targeting and other capabilities under the premise of an in-depth understanding of the evolution mechanism of biological barriers at all levels in various disease states in the body to overcome barriers at all levels in the body, so as to achieve efficient tumor targeted delivery.

Studies have shown that although the positively charged surface of the nanocarrier has a better adhesion to the cells with a certain negative charge on the surface and promotes cell uptake, however, in the blood circulation system in the body, the nanocarrier compounds with positive charges on the surface are easily combined with various opsonizing proteins, and then quickly cleared by the mononuclear macrophages through the liver and spleen. Therefore, by changing the surface charge of the nanocarrier, it is possible to reduce the clearance of the mononuclear macrophage system, extend the circulation time in the body, increase the rate of cell adhesion and uptake, and improve the lysosomal escape ability. In order to improve the efficiency of nanocarrier delivery to the tumor site, this contradiction between various levels of biological barriers must be overcome.

SUMMARY OF THE INVENTION

One of the purposes of the invention is to provide a preparation method of siRNA delivery system compound, comprising the following steps:

S1. adding cholesterol and Boc-protected histidine to dichloromethane, continuing to add dicyclohexylcarbodiimide and 4-dimethylaminopyridine to dichloromethane, reacting at room temperature for 14-16 h, successively filtering off the white precipitate, removing the solvent and purifying under decompression to obtain a Boc-protected histidine cholesteryl ester intermediate;

S2. dissolving the Boc-protected histidine cholesteryl ester intermediate prepared in S1 in dichloromethane, continuing to add trifluoroacetic acid, stirring for 1-1.5 h, then neutralizing with aqueous ammonia solution, evaporating the solvent under decompression, diluting the residue in ethyl acetate, washing and drying successively, and evaporating the solvent under decompression again to obtain a white powdery histidine cholesteryl ester intermediate;

S3. dissolving the histidine cholesteryl ester prepared in S2 in tetrahydrofuran to prepare a solution A, dissolving carboxymethyl chitosan, 1-ethyl-(3-dimethylaminopropyl) carbodiimide hydrochloride, and N-hydroxysuccinimide in a 1% acetic acid solution, activating at room temperature, adding solution A, reacting at room temperature for 70-72 h, evaporating tetrahydrofuran under decompression, then adding absolute ethanol to accumulate the precipitate, retaining the precipitate, and the precipitate is washed sequentially with tetrahydrofuran, acetone and ether to obtain a white powdery histidine cholesteryl ester modified carboxymethyl chitosan polymer compound;

S4. dissolving carbodiimide hydrochloride and N-hydroxysuccinimide in a targeted marker solution with a concentration of 0.1 mmol, activating the carboxyl group for 1-1.5 h to obtain an activated targeted marker solution, dissolving the histidine cholesteryl ester modified carboxymethyl chitosan prepared in S3 in a 0.8-1% hydrochloric acid solution, dripping the activated targeted marker solution under stirring, reacting for 22-24 h at 4° C., then freeze-drying to obtain a carboxymethyl chitosan polymer compound modified by histidine cholesteryl ester and the targeted marker;

S5. dissolving the carboxymethyl chitosan polymer compound modified by histidine cholesteryl ester and the targeted marker in a HEPES buffer solution with a concentration of 20 Mm and a pH value of 7.4, treating with ultrasonic, then purifying to obtain a nano spherical carrier;

S6. dissolving siRNA in a nano spherical carrier solution with a concentration of 0.56 mg/ml, and the ratio of siRNA to nano spherical carrier in the solution is 1 pmol: 0.01-0.2 ug, and storing in a dark place for more than 30 min to obtain a siRNA delivery system compound.

Further, in S1, the ratio of cholesterol, Boc-protected histidine, methylene chloride, dicyclohexylcarbodiimide and 4-dimethylaminopyridine is 200-220 mg: 125-135 mg: 10-12 mL: 1.8-2 mg;

in S2, the mass volume ratio of Boc-protected histidine cholesteryl ester intermediate, dichloromethane, trifluoroacetic acid and ammonia solution is 200-220 mg: 6-8 mL: 0.8-1 mL: 1.8-2 mL;

in S3, the mass volume ratio of histidine cholesteryl ester to tetrahydrofuran is 500-520 mg: 100 mL, and the mass volume ratio of carboxymethyl chitosan, 1-ethyl-(3-dimethylaminopropyl) carbodiimide hydrochloride, N-hydroxysuccinimide, A solution and absolute ethanol is 480-500 mg: 240-260 mg: 150-160 mg: 48-50 mL: 198-200 mL;

in S4, the mass volume ratio of carbodiimide hydrochloride, N-hydroxysuccinimide, targeted marker solution, cholesteryl histidine and hydrochloric acid solution is 38-40 mg: 22-23 mg: 1.8-2 mL: 40-42 mg: 10-12 mL;

in S5, the mass-volume ratio of the carboxymethyl chitosan polymer compound modified by histidine cholesteryl ester and the targeted marker and the HEPES buffer solution is 10-12 mg: 5-6 mL.

The second purpose of the invention is to provide a carboxymethyl chitosan polymer compound modified with histidine cholesteryl ester prepared by the preparation method.

Further, in S4, the targeted marker is EGFR monoclonal antibody, HER2 monoclonal antibody, PSMA monoclonal antibody, or RGD short peptide containing arginine, glycine and aspartic acid sequences.

The third purpose of the invention is to provide a carboxymethyl chitosan polymer compound modified by histidine cholesteryl ester and the targeted marker prepared by the preparation method.

The fourth purpose of the invention is to provide a multifunctional nano spherical carrier with active targeting and pH-responsive protonation prepared by the preparation method.

Furthermore, the siRNA silences genes related to tumorigenesis, proliferation, and metastasis.

The fifth purpose of the invention is to provide a siRNA delivery system compound prepared by the preparation method.

The sixth purpose of the invention is to provide an application of the siRNA delivery system compound, wherein the application is to deliver siRNA to malignant tumor cells.

In order to achieve the above purposes, the technical solutions of the invention are conceived as follows:

The invention provides a stable multifunctional siRNA delivery carrier with active targeting and pH response protonation and a preparation method thereof. The siRNA delivery carrier has suitable size, surface charge, good biocompatibility, and has multiple functions such as tumor targeting and environmental responsiveness changes, which can effectively overcome the complex biological barriers at all levels in the body to achieve high-efficiency and low-toxicity delivery purposes. The siRNA delivery carrier can not only effectively protect siRNA from being degraded by nucleases, but also can reduce the elimination of the mononuclear macrophage system in the body, extend the circulation time in the body, and increase the efficiency of cell uptake and the escape ability of intracellular lysosomes.

The siRNA delivery carrier of the invention is obtained by covalently coupling the biodegradable polymer compound carboxymethyl chitosan as the carrier backbone and the targeted marker as the side chain of the carrier and the amino acid cholesteryl ester; the polymer compound carboxymethyl chitosan, targeted marker and amino acid cholesteryl ester have reactive functional groups capable of covalent coupling; the polymer compound carboxymethyl chitosan has functional groups such as carboxyl group, amino group reaction, hydroxyl group, etc., and can be further modified with targeted markers and amino acid cholesteryl ester; the polymer compound carboxymethyl chitosan has the characteristics of being biodegradable, good biocompatibility, no cytotoxicity, etc.; the targeted marker has polypeptides or monoclonal antibodies that specifically adhere to and interact with tumor cells or tumor microenvironment; the amino acid cholesteryl ester is a compound formed by dehydration of histidine and cholesterol through an esterification reaction; the amino acid cholesteryl ester not only has a good hydrophobic ability, but also has a more sensitive pH-responsive protonation ability.

In the invention, the amino acid cholesteryl ester is modified to the side chain of carboxymethyl chitosan through amide reaction to give carboxymethyl chitosan hydrophobic ability and more sensitive pH-responsive protonation ability; the amino acid cholesteryl ester modified carboxymethyl chitosan can self-assemble into a nano spherical carrier with good stability in an aqueous solution with a lower critical micelle concentration; the amino acid cholesteryl ester modified carboxymethyl chitosan has a more sensitive pH response ability to protonate, and its self-assembled nano spherical carrier with good stability also has the ability of more sensitive pH-responsive protonation. The amino acid cholesteryl ester modified carboxymethyl chitosan is positively charged under neutral pH conditions, and has a strong binding ability with negatively charged siRNA, which can effectively entrap siRNA to form a nanocarrier compound, and protect the siRNA from degradation by nucleases in vivo; the entrapped siRNA-carrying nanocarrier compound has a more sensitive pH-responsive protonation ability.

In the invention, the more sensitive pH-responsive protonation can cause intracellular proton sponge action, which helps to improve the lysosome escape efficiency of the nanocarrier compounds formed by entrapping siRNA. In the invention, the targeted marker has specific adhesion to the antigen or receptor on the surface of tumor cells or the tumor microenvironment, which can target the delivery of the nanocarrier compounds containing siRNA to tumor tissues, and then improve the uptake efficiency of tumor cells through targeted receptor-mediated endocytosis; the targeted marker can be modified to the carboxymethyl chitosan backbone modified by amino acid cholesteryl ester by covalent coupling; the targeted marker is preferably EGFR monoclonal antibody, HER2 monoclonal antibody, PSMA monoclonal antibody, or RGD short peptide containing arginine, glycine and aspartic acid (Arg-Gly-Asp) sequences.

The compound of the invention adopts a novel hydrophilic carboxymethyl chitosan as the backbone and forms a long-chain amphoteric ester by modifying hydrophobic cholesterol, which can self-assemble into a nanocapsule-like structure to entrap siRNA at a lower critical micelle concentration, and has good stability.

The compound of the invention entraps siRNA in the form of vesicles, which not only protects the siRNA from nuclease hydrolysis and maintains the stability of the siRNA, but also make the compound have a better slow-release effect at the diseased part and achieve a higher utilization rate of siRNA.

The compound of the invention adopts EGFR monoclonal antibody, HER2 monoclonal antibody, PSMA monoclonal antibody, or RGD short peptide containing arginine, glycine and aspartic acid (Arg-Gly-Asp) sequences as the targeted marker modification, which can actively target the carrier compound to tumors and other lesions so as to have a better specific distribution.

The compound of the invention has histidine with imidazole group, and its physicochemical form has a sensitive dependence on pH. When the pH in the environment is lower, the degree of protonation is higher and the surface of the entire nanocarrier composite is positively charged. This effect can not only reduce the adhesion of various opsonins in the blood environment and reduce the phagocytosis of the mononuclear macrophage system, but also promote the uptake of nanocarrier compounds by the cells, and can further produce proton sponge effect in low pH lysosome to promote swelling and rupture of lysosome to release nanocarrier compounds.

DETAILED DESCRIPTION OF THE PREFERRED EMBODIMENTS

Figure 1:
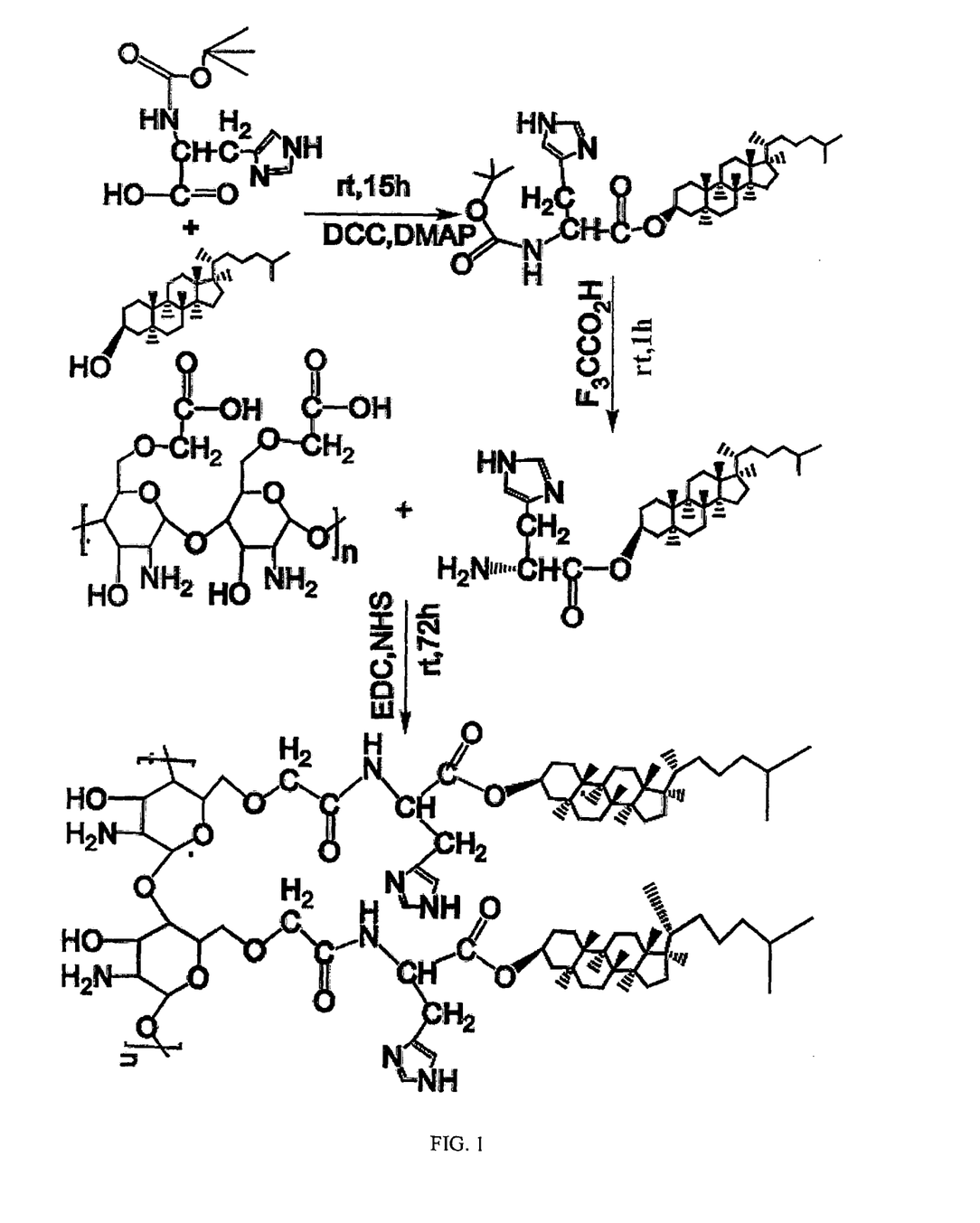
FIG. 1 is a chemical reaction equation for the synthesis of CHC in Embodiment 1.
Figure 2:
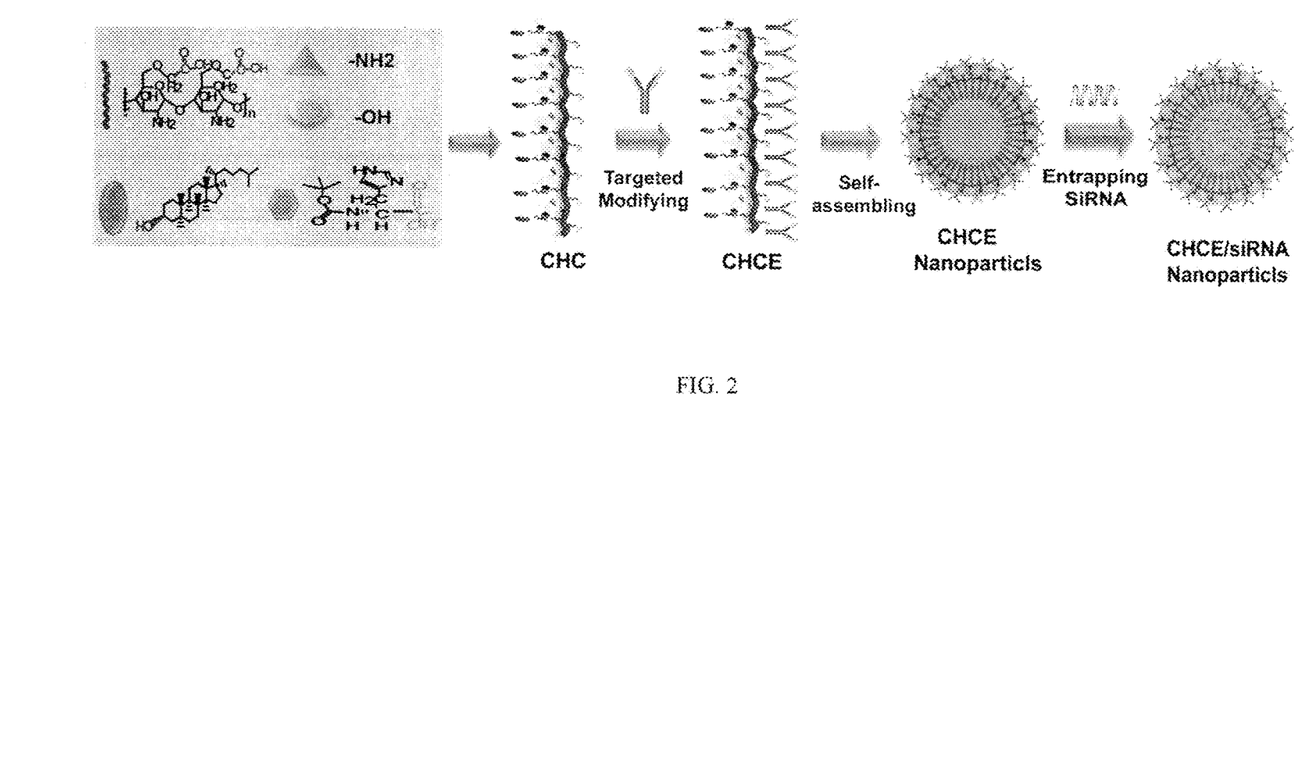
FIG. 2 is a schematic diagram of the synthesis of CHCE/siRNA in Embodiment 1.
Figure 3:
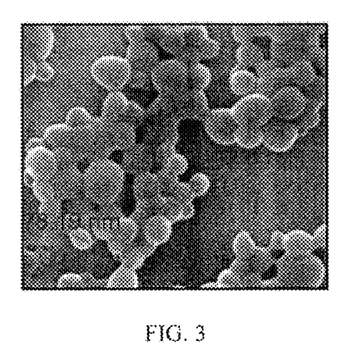
FIG. 3 shows the morphology and structure of the composite surface in Embodiment 1 detected by scanning electron microscopy; the sample is prepared and observed under the electron microscope with a 1 mg/ml delivery system compound aqueous solution, and the magnification is 150,000 times.
Figure 4:
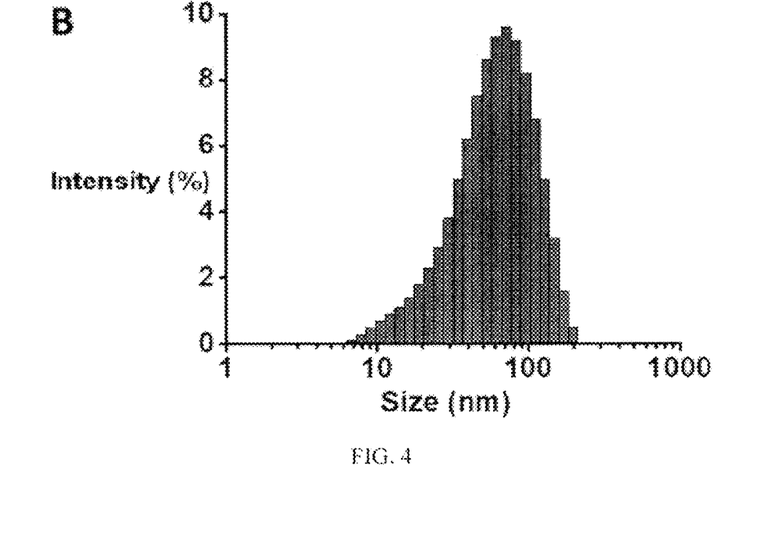
FIG. 4 shows the particle size distribution of the delivery system compound in Embodiment 1 detected by the Malvern particle size analyzer; the detection solution is a 1 mg/ml nanocarrier compound aqueous solution, and the detection temperature is 25° C.
Figure 5:
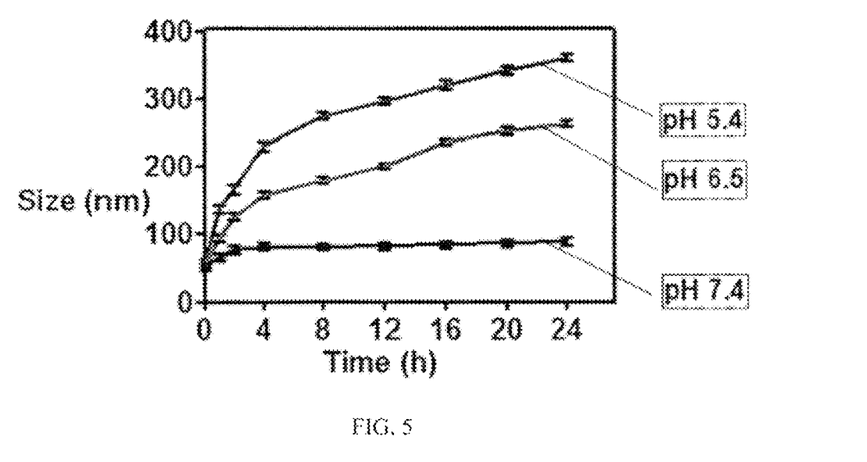
FIG. 5 shows the changes in particle size of the delivery system compound in Embodiment 1 detected by the Malvern particle size analyzer in PBS buffers of different pH values.
Figure 6:
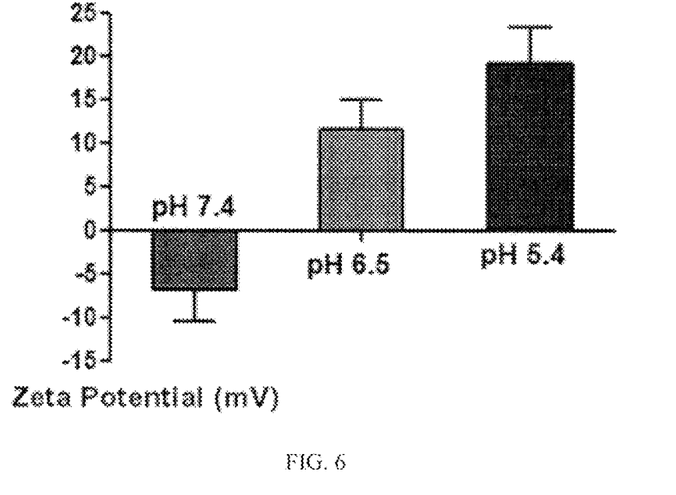
FIG. 6 shows the surface charge changes of the delivery system compound in Embodiment 1 detected by the Malvern Particle Sizer in PBS buffers of different pH values.
Figure 7:
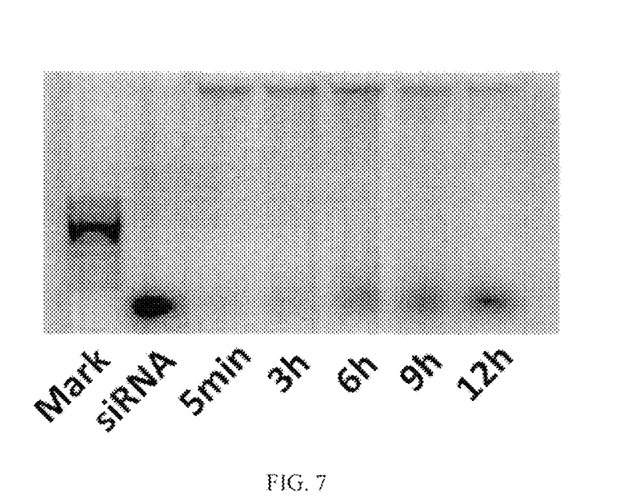
FIG. 7 shows the stability of the delivery system compound in Embodiment 1 in 50% serum at 37° C. in the electrophoresis gel test; the dissociated siRNA is positioned and quantified against the pure siRNA band (the first lane), the dissociation is slow, and the half-life period is about 12 hours.
Figure 8:
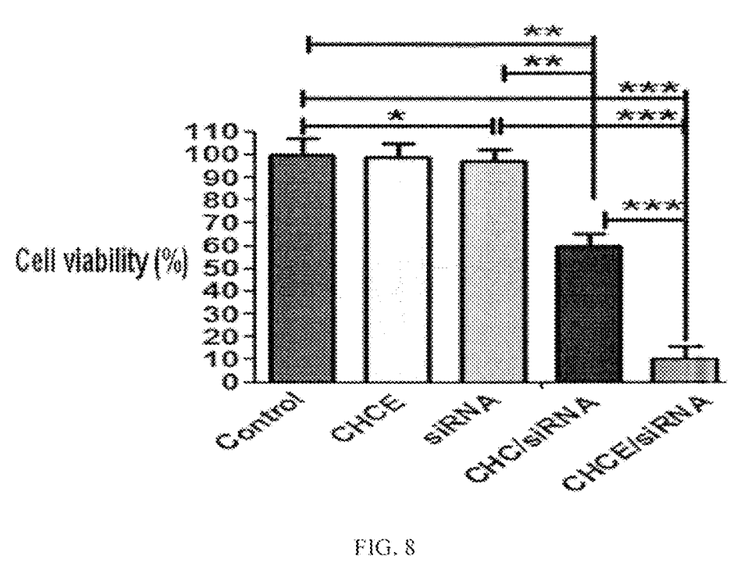
FIG. 8 shows the proliferation detection of cells in each group (mean±sem, n=3); *p<0.05, p<0.05, *p<0.05.

The invention will be described in detail hereinafter with reference to the drawings and specific embodiments, but it should not be understood as a limitation of the invention. Unless otherwise specified, the technical means used in the following embodiments are conventional means well known to those skilled in the art. The materials, reagents, etc. used in the following embodiments can be obtained from commercial sources unless otherwise specified.

Embodiment 1

A preparation method of siRNA delivery system compound, comprising the following steps:

S1. synthesis of a Boc-protected histidine cholesteryl ester intermediate (Boc-CH);

adding 200 mg cholesterol and 130 mg (0.52 mmol) Boc-protected histidine to 10 mL dichloromethane, continuing to add 140 mg (0.68 mmol) dicyclohexylcarbodiimide (DCC) and 2 mg (0.016 mmol) 4-dimethylaminopyridine (DMAP) to dichloromethane, reacting at room temperature for 15 h, successively filtering off the white precipitate, removing the solvent and purifying under decompression, purifying by thin chromatography and column chromatography with ethyl acetate/petroleum ether (with a volume ratio of 1:4) to obtain a Boc-protected histidine cholesteryl ester intermediate (Boc-CH);

S2. synthesis of a histidine cholesteryl ester intermediate (CH);

dissolving 200 mg Boc-CH prepared in S1 in 7 mL dichloromethane, continuing to add 1 ml (13.5 mmol) trifluoroacetic acid, stirring for 1 h, then neutralizing with 2 ml of 36.6% aqueous ammonia solution, evaporating the solvent under decompression, diluting the residue in ethyl acetate, washing with water, drying with magnesium sulfate, and evaporating the solvent under decompression again to obtain a white powdery histidine cholesteryl ester intermediate (CH);

S3. synthesis of a histidine cholesteryl ester modified carboxymethyl chitosan polymer compound (CHC);

dissolving 520 mg (1.0 mmol) CH prepared in S2 in 100 ml tetrahydrofuran to prepare a solution A;

dissolving 500 mg carboxymethyl chitosan, 250 mg 1-ethyl-(3-dimethylaminopropyl) carbodiimide hydrochloride, and 150 mg (1.3 mmol) N-hydroxysuccinimide (NHS) in a 50 ml 1% acetic acid solution, activating carboxyl group at room temperature for 1 h, adding solution A while stirring, reacting at room temperature for 72 h, evaporating tetrahydrofuran under decompression, then adding 200 ml of absolute ethanol and stirring to accumulate the precipitate, filtering, and the precipitate is washed sequentially with tetrahydrofuran, acetone and ether to obtain a white powdery histidine cholesteryl ester modified carboxymethyl chitosan polymer compound (CHC);

S4. synthesis of a carboxymethyl chitosan polymer compound modified by histidine cholesteryl ester and the targeted marker (CHCE);

dissolving 38 mg (0.2 mmol) EDC.HCL and 23 mg (0.2 mmol) NHS in 2 ml EGFR monoclonal antibody solution with a concentration of 0.1 mmol, activating the carboxyl group for 1 h to obtain an activated targeted marker solution, dissolving 40 mg CHC solution prepared in S3 in 10 mL 1% hydrochloric acid solution, dripping the activated targeted marker solution under stirring, reacting for 24 h at 4° C., then freeze-drying to obtain a carboxymethyl chitosan polymer compound modified by histidine cholesteryl ester and the targeted marker (CHCE);

S5. synthesis of a multifunctional nanocarrier with active targeting and pH-responsive protonation;

dissolving 10 mg carboxymethyl chitosan polymer compound modified by histidine cholesteryl ester and the targeted marker in 5 ml HEPES buffer solution with a concentration of 20 Mm and a pH value of 7.4, treating with ultrasonic for 2 min, repeating the ultrasonic treatment step 3 times, then purifying with a 3000 molecular weight dialysis bag in 1.5 L double pure water for 24 h to obtain a nano spherical carrier;

S6. synthesis of a delivery system compound (CHCE/siRNA);

dissolving siRNA in a nano spherical carrier solution with a concentration of 0.56 mg/ml, and the ratio of siRNA to nano spherical carrier in the solution is 1 pmol: 0.1 ug, and storing in a dark place for more than 30 min to obtain a siRNA delivery system compound.

The target gene of siRNA silencing in the embodiment is the VEGFR gene, which has an important promoting effect on tumorigenesis, proliferation, and metastasis. The base sequence of the siRNA in the embodiment is 5'-UGG AUU UGU ACC AUU CUU CUG-3', as shown in SEQ ID NO. 1. Determination of the Properties of the Above Compound 1. Detecting the morphology of the nanocarrier compound by transmission electron microscope: taking 2 microliters of the compound dissolved droplets on the silicon wafer to dry naturally, metal spraying for 10 s, and observing under the scanning electron microscope. The result is shown in FIG. A, and it can be seen from the scanning electron micrograph that the prepared compound is spherical and has a relatively stable structure; after the Malvern particle size analyzer detects its particle size distribution, the result of FIG. B shows that the average particle size of the composite is about 80 nm.

2. Detecting the particle size distribution of the compound at a predetermined time point after being diluted in a PBS solution of a pH value of 7.4, 6.5 or 5.4, and the result is shown in FIG. C; it can be seen from the results that the compound has a stable particle size in a PBS solution with a pH of 7.4, and there is no huge change with time; when the pH is 6.5 or 5.4, the particle size of the compound changes greatly with time. At 24 h, the particle size of the compound with a pH value of 6.5 increased to about 220 nm, and the particle size of the compound with a pH value of 5.4 increased to about 350 nm.

3. Detecting the surface charge of the compound in the PBS solution with a PH value of 7.4, 6.5 or 5.4, and the result is shown in FIG. D; the result shows that when the pH value of the compound is 7.4, its surface Zeta charge is about −6.9 mv; when the pH value is 6.5, the surface zeta charge is about 11.4 mv; when the pH value is 5.4, the surface zeta charge is about 19.1 mv. It shows that as the pH value of the environment becomes smaller and the acidity increases, the protonation degree of the compound becomes deeper, and the positive charge of Zeta on the compound surface becomes larger.

4. Serum stability of the compound: stability test of siRNA and compound in 50% serum at different time points; incubating the siRNA and the compound in 50% nude mouse serum at 37° C. Collecting 5 μl (10 pmol siRNA equivalent) aliquots at different time points (5 min, 3 h, 6 h, 9 h, 12 h) and probing on a 1% agarose gel, and obtaining the gel image with a fluorescence imaging system. The results are shown in FIG. E, and the results show that the compound dissociates very slowly, and the half-life period is about 12 h, which proves that the compound of the invention can well protect siRNA from nuclease enzymatic hydrolysis.

5. Cell Proliferation Detection

Inoculating SK28 cells (malignant melanoma) (1×104 cells/well) in a 96-well microplate and standing for 24 h. PBS, CHCE, siRNA, CHC/siRNA, CHCE/siRNA (the experimental siRNA concentration is 100 nM) nanoparticles are added to 3 different wells. After incubating for 72 h, adding MTT solution (Sigma) to each well and incubating at 37° C. for 1 h. Removing the medium containing MTT, and adding 200 mL DMSO solution to dissolve the azo crystals formed by living cells. Recording the optical density at 570 nm with a microplate reader, and calculating the cell survival rate as the percentage of untreated control cells. The results are shown in FIG F, and the results show that compared to the blank control PBS group, the carrier-only CHCE group and the siRNA-only group have no inhibitory effect on cell proliferation; the non-targeting modified CHC/siRNA group and the targeting modified CHCE/siRNA group has an inhibitory effect on cell proliferation, and the targeting modified CHCE/siRNA group has a higher inhibitory effect on cell proliferation than the CHC/siRNA group without targeted modification, which proves that the nanocarrier compound can effectively inhibit the proliferation of tumor cells.

Embodiment 2

The embodiment provides a compound, wherein the preparation conditions are the same as those in Embodiment 1, except that the targeted marker solution is changed to PSMA monoclonal antibody solution, and siRNA is a sequence that silences genes related to the occurrence, proliferation, and metastasis of prostate cancer cells; finally, a siRNA delivery system compound targeting prostate cancer is synthesized.

Embodiment 3

The embodiment provides a compound, wherein the preparation conditions are the same as those in Embodiment 1, except that the targeted marker solution is changed to HER2 monoclonal antibody solution, and siRNA is a sequence that silences genes related to the occurrence, proliferation, and metastasis of breast cancer cells; finally, a siRNA delivery system compound targeting breast cancer is synthesized.

Embodiment 4

The embodiment provides a compound, wherein the preparation conditions are the same as those in Embodiment 1, except that the targeted marker solution is changed to RGD short peptide containing arginine, glycine and aspartic acid (Arg-Gly-Asp) sequences, and siRNA are sequences that silence genes related to the occurrence, proliferation, and metastasis of triple negative breast cancer, non-small cell lung cancer, glioblastoma or osteosarcoma, respectively; finally, siRNA delivery system compounds targeting triple negative breast cancer, non-small cell lung cancer, glioblastoma or osteosarcoma are synthesized.

It should be noted that when the claims of the invention involve numerical ranges, it should be understood that the two end points of each numerical range and any value between the two end points can be selected. To prevent redundancy, the invention describes preferred embodiments.

Although the preferred embodiments of the invention have been described, those skilled in the art can make additional variations and modifications to these embodiments once they learn the basic creative concept. Therefore, the appended claims are intended to be interpreted as including the preferred embodiments and all changes and modifications falling within the scope of the invention.

Obviously, those skilled in the art can make many variations and modifications to the invention without departing from the spirit and scope of the invention. In this way, if these variations and modifications of the invention fall within the scope of the claims of the invention and the equivalent technologies thereof, the invention is also intended to include these variations and modifications.

The invention claimed is:

1. A preparation method of a siRNA delivery system compound, comprising the following steps:
   S1: adding cholesterol and Boc-protected histidine to dichloromethane, continuing to add dicyclohexylcarbodiimide and 4-dimethylaminopyridine to the dichloromethane, reacting at room temperature for 14-16 h, successively filtering off a white precipitate, removing a solvent and purifying under decompression to obtain a Boc-protected histidine cholesteryl ester intermediate;
   S2: dissolving the Boc-protected histidine cholesteryl ester intermediate prepared in S1 in dichloromethane, continuing to add trifluoroacetic acid, stirring for 1-1.5 h, then neutralizing with an aqueous ammonia solution, evaporating a solvent under decompression, diluting a residue in ethyl acetate, washing and drying successively, and evaporating the solvent under decompression again to obtain a white powdery histidine cholesteryl ester intermediate;
   S3: dissolving the histidine cholesteryl ester prepared in S2 in tetrahydrofuran to prepare a solution A, dissolving carboxymethyl chitosan, 1-ethyl-(3-dimethylaminopropyl) carbodiimide hydrochloride, and N-hydroxysuccinimide in a 1% acetic acid solution, activating at room temperature, adding the solution A, reacting at room temperature for 70-72 h, evaporating tetrahydrofuran under decompression, then adding absolute ethanol to accumulate a precipitate, retaining the precipitate, and washing the precipitate sequentially with tetrahydrofuran, acetone and ether to obtain a white powdery histidine cholesteryl ester modified carboxymethyl chitosan polymer compound;
   S4: dissolving carbodiimide hydrochloride and N-hydroxysuccinimide in a targeted marker solution with a concentration of 0.1 mmol, activating the carboxyl group for 1-1.5 h to obtain an activated targeted marker solution, dissolving the histidine cholesteryl ester modified carboxymethyl chitosan polymer compound prepared in S3 in a 0.8-1% hydrochloric acid solution, dripping the activated targeted marker solution under stirring, reacting for 22-24 h at 4° C., then freeze-drying to obtain a carboxymethyl chitosan polymer compound modified by the histidine cholesteryl ester and the targeted marker;
   S5: dissolving the carboxymethyl chitosan polymer compound modified by the histidine cholesteryl ester and the targeted marker in a HEPES buffer solution with a concentration of 20 mM and a pH value of 7.4, treating with ultrasonic, then purifying to obtain a nano spherical carrier; and
   S6: dissolving siRNA in a nano spherical carrier solution with a concentration of 0.56 mg/mL, and the ratio of the siRNA to the nano spherical carrier in the solution is 1 pmol: 0.01-0.2 μg, and storing in a dark place for more than 30 min to obtain the siRNA delivery system compound.

2. The preparation method according to claim 1, wherein in S1, the ratio of the cholesterol, the Boc-protected histidine, the dichloromethane, the dicyclohexylcarbodiimide and the 4-dimethylaminopyridine is 200-220 mg: 125-135 mg: 10-12 mL: 1.8-2 mg;
   in S2, the mass volume ratio of the Boc-protected histidine cholesteryl ester intermediate, the dichloromethane, the trifluoroacetic acid and the aqueous ammonia solution is 200-220 mg: 6-8 mL: 0.8-1 mL: 1.8-2 mL;
   in S3, the mass volume ratio of the histidine cholesteryl ester to the tetrahydrofuran is 500-520 mg: 100 mL, and the mass volume ratio of the carboxymethyl chitosan, the 1-ethyl-(3-dimethylaminopropyl) carbodiimide hydrochloride, the N-hydroxysuccinimide, the solution A and the absolute ethanol is 480-500 mg: 240-260 mg: 150-160 mg: 48-50 mL: 198-200 mL;
   in S4, the mass volume ratio of the carbodiimide hydrochloride, the N-hydroxysuccinimide, the targeted marker solution, the cholesteryl histidine ester modified carboxymethyl chitosan polymer compound and the hydrochloric acid solution is 38-40 mg: 22-23 mg: 1.8-2 mL: 40-42 mg: 10-12 mL;
   in S5, the mass-volume ratio of the carboxymethyl chitosan polymer compound modified by the histidine cholesteryl ester and the targeted marker and the HEPES buffer solution is 10-12 mg: 5-6 mL.

3. The preparation method according to claim 2, wherein in S4, the targeted marker is one selected from the group consisting of EGFR monoclonal antibody, HER2 monoclonal antibody, PSMA monoclonal antibody, or RGD short peptide containing arginine, glycine and aspartic acid sequences.

4. The preparation method according to claim 3, wherein the siRNA silences genes related to tumorigenesis, proliferation, and metastasis.

* * * * *